United States Patent [19]

Krüger et al.

[11] Patent Number: 4,965,286
[45] Date of Patent: Oct. 23, 1990

[54] AGENTS FOR REPELLING INSECTS AND MITES

[75] Inventors: Bernd W. Krüger; Klaus Sasse, both of Gladbach; Winfried Lunkenheimer, Bayerwerk; Franz P. Hoever, Bayerwerk; Günther Nentwig, Bayerwerk; Wolfgang Behrenz, Overath, all of Fed. Rep. of Germany

[73] Assignee: Bayer Aktiengesellschaft, Leverkusen, Fed. Rep. of Germany

[21] Appl. No.: 356,480

[22] Filed: May 24, 1989

[30] Foreign Application Priority Data

Jun. 16, 1988 [DE] Fed. Rep. of Germany ....... 3820528

[51] Int. Cl.$^5$ .................... A01N 47/40; A01N 47/46; A01N 47/48
[52] U.S. Cl. ............................ 514/514; 424/DIG. 10
[58] Field of Search ..................... 514/613, 561, 514; 424/DIG. 10

[56] References Cited

U.S. PATENT DOCUMENTS 4,367,344  1/1983  Gallenkamp ..................... 560/115
4,554,017  11/1985  Schroder et al. ................. 71/113

FOREIGN PATENT DOCUMENTS 222104  3/1987  Japan ................................ 514/613

Primary Examiner—Douglas W. Robinson
Assistant Examiner—Kevin E. Weddington
Attorney, Agent, or Firm—Sprung, Horn, Kramer & Woods

[57] ABSTRACT

A insect and mite repellent composition in which the active ingredient is an acylated α-amine acid ester derivative of the formula

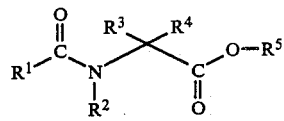

in which
$R^1$ stands for hydrogen or for an optionally substituted alkyl, alkenyl or alkinyl radical,
$R^2$ and $R^5$ are identical or different and stand for optically substituted alkyl, alkenyl or alkinyl radicals and
$R^3$ and $R^4$ stand for hydrogen or optionally substituted alkyl, aralkyl or aryl, or together with the atom to which they are bonded form an optionally substituted, monocyclic ring.

6 Claims, No Drawings

AGENTS FOR REPELLING INSECTS AND MITES

The present invention relates to the use of acylated α-amino acid ester derivatives, some of which are known, as agents which repulse insects and mites.

Agents which repel insects and mites (repellents) have the purpose of preventing noxious or unpleasant arthropods from touching, and from stinging and sucking or biting on surfaces to which they are attracted, for example the skin of animals and humans, if the former have previously been treated with such agents.

A number of active compounds has already been suggested as repellents (cf., for example, K. H. Büchel in Chemie der Pflanzenschutz- und Schädlingsbekämpfungsmittel [Chemistry of Plant Protection Agents and Pesticides]; editor: R. Wegler, Vol. 1, Springer Verlag Berlin, Heidelberg, New York, 1970 p. 487 et seq.).

N-Diethyl-3-methyl-benzamide (DEET), dimethyl phthalate and 2-ethyl-hexane-1,3-diol, of which especially DEET has gained considerable importance in practice, are particularly well known and have been in use for some time [see, for example, R. K. Kocher, R. S. Dixit, C. I. Somaya; Indian J. Med. Res. 62, 1 (1974)].

A considerable disadvantage of the known repellents is their insufficient long-lasting action which is relatively short in some cases (only some hours).

Some of the compounds defined by formula (I) below are known (cf., for example, EP-OS (European Published Specification No.) 136,615 corresponding to CA-Patent No. 1,241,966 and EP-OS (European Published Specification No.) 221,502 corresponding to South African Patent No. 86-8426.

However, nothing has been known to date about an insect- and mite-repellent action.

It has now been found that the acylated α-amino acid ester derivatives, some of which are known, of the formula

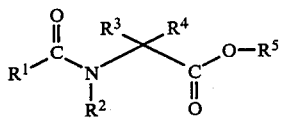

(I)

in which
R$^1$ stands for hydrogen or for an optionally substituted alkyl, alkenyl or alkinyl radical,
R$^2$ and R$^5$ are identical or different and stand for optionally substituted alkyl, alkenyl or alkinyl radicals and
R$^3$ and R$^4$ stand for hydrogen or optionally substituted alkyl, aralkyl or aryl, or together with the atom to which they are bonded form an optionally substituted, monocyclic ring, possess a powerful insect- and mite-repellent action.

The repellent action is considerably better than that of the repellents known from the prior art. The active compounds according to the invention thus represent a valuable enrichment of the art.

The present invention thus relates to the use of acylated α-amino acid ester derivatives of the general formula (I) for repulsing insects and mites.

Furthermore, the invention relates to insect- and mite-repellent agents, characterized in that they contain at least one acylated α-amino acid ester derivative of the general formula (I).

The agents according to the invention, which contain at least one derivative of the formula (I), can also contain further agents which repulse insects. These include virtually all customary repellents (cf., for example, K. H. Büchel in Chemie der Pflanzenschutz- und Schädlingsbekämpfungsmittel [Chemistry of Plant Protection Agents and Pesticides]; editor: R. Wegler, Vol. 1, Springer Verlag Berlin, Heidelberg, New York, 1970 p. 487 et seq.).

In the case of repellent combinations, it is preferred to use the acylated α-amino acid esters of the general formula (I) together with repellent carboxamides, 1,3-alkanediols and acyl esters. Substances which may be mentioned individually are: N-diethyl-3-methyl-benzamide (DEET), 2-ethyl-1,3-hexanediol (Rutgers 612) and dimethyl phthalate.

The general formula (I) gives a characterization of the acylated α-amino acid ester derivatives to be used according to the invention.

Preferably, the radicals given in formula (I) have the following meaning.

The optionally substituted alkyl group in the radicals R$^1$ and R$^5$ is straight-chain or branched and contains 1 to 12, preferably 1 to 10, and in particular 1 to 5, carbon atoms. examples which may be mentioned are methyl, ethyl, n- or i-propyl, n-, i- and t-butyl and n-pentyl.

Optionally substituted alkenyl represents straight-chain or branched alkenyl, preferably having 2 to 10, in particular 2 to 7, carbon atoms. Examples which may be mentioned are optionally substituted ethenyl, prop-1-enyl, prop-2-enyl, but-1-enyl, but-2-enyl and but-3-enyl.

Together with the atom to which they are bonded, the radicals R$^3$ and R$^4$ can form a 3- to 7-membered, saturated ring which can be substituted by 1 or 2, preferably one, alkyl group, in particular methyl.

Optionally substituted alkinyl represents straight-chain or branched alkinyl, preferably having 2 to 8, in particular 2 to 5, carbon atoms. Examples which may be mentioned are optionally substituted ethinyl, 2-propinyl, 2-butinyl, 3-butinyl and 1-methyl-2-propinyl.

The optionally substituted radicals R$^1$ to R$^5$ can carry one or more, preferably 1 to 3, in particular 1 or 2, identical or different substituents. Substituents which may be mentioned are: alkyl preferably having 1 to 10, in particular 1 to 6, carbon atoms, such as methyl, ethyl, n- and i-propyl, n-, i- and t-butyl.

Compounds of the general formula (I) which are preferably used as repellents are those in which
R$^1$ stands for hydrogen, (C$_1$–C$_{10}$)-alkyl, (C$_2$–C$_{10}$)-alkenyl or (C$_2$–C$_{10}$)-alkinyl,
R$^2$ and R$^5$ are identical or different and stand for (C$_1$–C$_{10}$)-alkyl, (C$_2$–C$_{10}$)-alkenyl or (C$_2$–C$_{10}$)-alkinyl and
R$^3$ and R$^4$ stand for hydrogen, (C$_1$–C$_{10}$)-alkyl, for aryl or aralkyl, each of which is optionally substituted in the aryl moiety by one to three identical or different substituents, and each of which has 6 to 10 carbon atoms in the aryl moiety and if appropriate 1 to 4 carbon atoms in the alkyl moiety, suitable aryl substituents in each case being: halogen, in each case straight-chain or branched (C$_1$–C$_4$)-alkyl, (C$_1$–C$_4$)-halogenoalkyl, (C$_1$–C$_4$)-halogenoalkoxy and (C$_1$–C$_4$)-halogenoalkylthio, or, together with the atom to which they are bonded, stand for cycloalkyl having 3 to 7 carbon atoms.

Compounds of the general formula (I) which are particularly preferably used as repellents are those in which $R^1$ stands for hydrogen, ($C_1$–$C_5$)-alkyl, ($C_2$–$C_5$)-alkenyl or ($C_2$–$C_5$)-alkinyl, $R^2$ stands for ($C_1$–$C_5$)-alkyl, ($C_2$–$C_5$)-alkenyl or ($C_2$–$C_5$)-alkinyl, $R^3$ and $R^4$ stand for hydrogen, ($C_1$–$C_5$)-alkyl, for phenyl or phenylalkyl which have, if appropriate, 1 or 2 carbon atoms in the alkyl moiety and each of which is optionally substituted in the phenyl moiety by one to three identical or different substituents, suitable phenyl substituents in each case being: fluorine, chlorine, bromine, ($C_1$–$C_2$)-alkyl, ($C_1$–$C_2$)-halogenoalkyl, ($C_1$–$C_2$)-halogenoalkoxy, ($C_1$–$C_2$)-halogenoalkylthio or, together with the atom to which they are bonded, stand for cycloalkyl having 3 to 6 carbon atoms and $R^5$ stands for ($C_1$–$C_{10}$)-alkyl, ($C_2$–$C_5$)-alkenyl or ($C_2$–$C_5$)-alkinyl.

Compounds of the formula (I) which are very particularly preferred are those in which $R^1$ stands for hydrogen, ($C_1$–$C_5$)-alkyl, ($C_2$–$C_5$)-alkenyl or ($C_2$–$C_5$)-alkinyl, $R^2$ stands for ($C_1$–$C_5$)-alkyl, ($C_2$–$C_5$)-alkenyl or ($C_2$–$C_5$)-alkinyl, $R^3$ and $R^4$ stand for hydrogen or ($C_1$–$C_5$)-alkyl, or for phenyl, benzyl or phenethyl, each of which is optionally substituted in the phenyl moiety by one to three identical or different substituents, suitable substituents in each case being: fluorine, chlorine, bromine, methyl, ethyl, trifluoromethyl, trifluoromethoxy, trifluoromethylthio or together with the atom to which they are bonded stand for cyclopropyl, cyclopentyl or cyclohexyl and $R^5$ stands for ($C_1$–$C_{10}$)-alkyl, ($C_2$–$C_5$)-alkenyl or ($C_2$–$C_5$)-alkinyl.

Furthermore, compounds of the formula (I) which are very particularly preferably used are those in which $R^1$ stands for hydrogen, ($C_1$–$C_5$)-alkyl or ($C_2$–$C_5$)-alkenyl, $R^2$ stands for ($C_1$–$C_5$)-alkyl or ($C_2$–$C_5$)-alkenyl, $R^3$ and $R^4$ stand for hydrogen, ($C_1$–$C_5$)-alkyl or together with the atom to which they are bonded for cyclopropyl and $R^5$ stands for ($C_1$–$C_5$)-alkyl or ($C_2$–$C_5$)-alkenyl.

As examples of the compounds of the formula (I) to be used according to the invention, there may be mentioned butyl N-acetyl-2-butylaminoacetate and ethyl N-but-2-enylform-amido-cyclopropanecarboxylate.

Due to their excellent insect- and mite-repellent action, these compounds are very particularly preferred.

In addition to the previously mentioned examples and those listed in the Preparation Examples, the following may also be mentioned. General formula

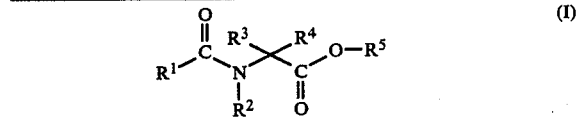

| $R^1$ | $R^2$ | $R^3$ | $R^4$ | $R^5$ |
|---|---|---|---|---|
| $CH_3$ | n-$C_4H_9$ | H | H | $C_2H_5$ |
| $CH_3$ | n-$C_4H_9$ | H | H | n-$C_4H_9$ |
| H | n-$C_4H_9$ | H | H | n-$C_4H_9$ |
| H | n-$C_4H_9$ | H | H | $C_2H_5$ |
| n-$C_4H_9$ | $CH_3$ | H | H | $C_2H_5$ |
| n-$C_4H_9$ | $CH_3$ | H | H | n-$C_4H_9$ |
| $CH_3$ | n-$C_4H_9$ | $CH_3$ | H | $C_2H_5$ |
| $CH_3$ | n-$C_4H_9$ | $CH_3$ | H | n-$C_4H_9$ |
| n-$C_4H_9$ | $CH_3$ | $CH_3$ | H | $C_2H_5$ |

-continued

| $R^1$ | $R^2$ | $R^3$ | $R^4$ | $R^5$ |
|---|---|---|---|---|
| n-$C_4H_9$ | $CH_3$ | $CH_3$ | H | n-$C_4H_9$ |
| $C_2H_5$ | n-$C_4H_9$ | H | H | $C_2H_5$ |
| n-$C_4H_9$ | $C_2H_5$ | H | H | n-$C_4H_9$ |
| $C_2H_5$ | n-$C_4H_9$ | $CH_3$ | H | $C_2H_5$ |
| $C_2H_5$ | n-$C_4H_9$ | $CH_3$ | H | n-$C_4H_9$ |
| n-$C_4H_9$ | $C_2H_5$ | $CH_3$ | H | $C_2H_5$ |
| n-$C_4H_9$ | $C_2H_5$ | $CH_3$ | H | n-$C_4H_9$ |
| $CH_3$ | n-$C_4H_9$ | $C_2H_5$ | H | $C_2H_5$ |
| $C_2H_5$ | n-$C_4H_9$ | $C_2H_5$ | H | n-$C_4H_9$ |
| n-$C_4H_9$ | $CH_3$ | $C_2H_5$ | H | $C_2H_5$ |
| n-$C_4H_9$ | $CH_3$ | $C_2H_5$ | H | n-$C_4H_9$ |
| n-$C_4H_9$ | $C_2H_5$ | $C_2H_5$ | H | $C_2H_5$ |
| n-$C_4H_9$ | $C_2H_5$ | $C_2H_5$ | H | n-$C_4H_9$ |
| $CH_3$ | n-$C_4H_9$ | H | H | $CH(CH_3)C_2H_5$ |
| $CH_3$ | $CH_3$ | H | H | $CH(CH_3)C_2H_5$ |
| $CH(CH_3)C_2H_5$ | $CH_3$ | H | H | $C_2H_5$ |
| $CH(CH_3)C_2H_5$ | $CH_3$ | H | H | n-$C_4H_9$ |
| $CH_3$ | $CH_3$ | H | H | t-$C_4H_9$ |
| $CH_3$ | $CH(CH_3)C_2H_5$ | H | H | $C_2H_5$ |
| $CH_3$ | $CH(CH_3)C_2H_5$ | H | H | $CH_3$ |
| H | $CH(CH_3)C_2H_5$ | H | H | n-$C_4H_5$ |
| H | $CH_3$ | —$CH_2$—$CH_2$— | | $CH(CH_3)C_2H_5$ |
| $CH_2CH=CH_2$ | $CH_3$ | H | H | n-$C_4H_9$ |
| $CH_3$ | $CH_2CH=CH_2$ | H | H | n-$C_4H_9$ |

Some of the acylated α-amino acid esters of the formula (I) to be used according to the invention are known and/or can be prepared by the processes known per se (cf. EP-OS (European Published Specification No.) 136,615 corresponding to CA-Patent No. 1,241,966 and DE-OS (German Published Specification No.) 3,539,307).

Accordingly, the compounds of the formula (I) are obtained when (A) the substituted amino-carboxylic acid esters, which are known per se or can be prepared by known processes (cf. EP-OS (European Published Specification No.) 5,782, corresponding to U.S. Pat. No. 4,554,017, EP-OS (European Published Specification No.) 25,141 corresponding to U.S. Pat. No. 4,367,344 and Cesare Ferri, Reaktionen der organischen Synthese (Reactions in Organic Synthesis), Georg Thieme Verlag Stuttgart, 1989, p. 446–452), of the formula $$\begin{array}{c} R^3 \quad R^4 \\ H_2N-C-C-O-R^5 \\ \parallel \\ O \end{array} \quad (II)$$

in which $R^3$, $R^4$ and $R^5$ have the abovementioned meaning, are initially reacted with acyl chlorides, which are known per se, of the formula (III)

$$R^1-\underset{\underset{O}{\parallel}}{C}-Cl \quad (III)$$

where $R^1$ has the meaning given under formula (I), if appropriate in the presence of an acid acceptor, such as, for example, triethylamine or potassium carbonate, and if appropriate using a diluent, such as, for example, toluene, $CH_2Cl_2$, tetrahydrofuran or acetonitrile, at temperatures between −40° C. and 110° C., and the reaction product is then reacted, in a second reaction step, if appropriate after isolation of the intermediate of the formula

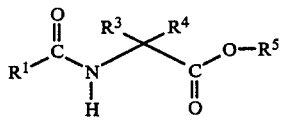 (IV)

in which
R¹, R³, R⁴ and R⁵ have the abovementioned meaning, with halides of the formula

 (V)

in which
R² has the abovementioned meaning and
X stands for chlorine, bromine or iodine, preferably for bromine and iodine,
if appropriate in the presence of an acid acceptor, such as, for example, triethylamine or potassium carbonate, or a base such as sodium hydride, if appropriate in the presence of a phase transfer catalyst, if appropriate using a diluent, such as, for example, toluene, tetrahydrofuran or acetonitrile, at temperatures between 0° and 110° C.

or the compounds of the formula (I) are obtained when (B) α-halogenocarboxylic acid esters of the formula

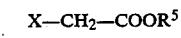 (VI)

in which
R⁵ has the abovementioned meaning and
X stands for chlorine, bromine or iodine, preferably for bromine or iodine,
are reacted with amines of the formula

 (VII)

in which
R² has the abovementioned meaning,
if appropriate in the presence of an acid acceptor such as, for example, triethylamine or potassium carbonate or a base such as sodium hydride, if appropriate using an organic diluent, such as, for example, toluene, tetrahydrofuran or acetonitrile, preferably at temperatures between 0° and 110° C. (cf., for example, Cesare Ferri, Reaktionen der organischen Synthese [Reactions of Organic Synthesis], Georg Thieme Verlag Stuttgart, 1978, p. 506-509), and the reaction product is then reacted in a second reaction step, if appropriate after isolation of the intermediate of the formula

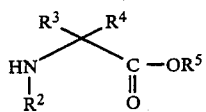 (VIII)

in which
R², R³, R⁴ and R⁵ have the abovementioned meaning, with acyl chlorides, which are known per se, of the formula

 (III)

where
R¹ has the meaning given under formula (I), if appropriate in the presence of an acid acceptor, such as, for example, triethylamine or potassium carbonate, and if appropriate using a diluent, such as, for example, toluene, $CH_2Cl_2$, tetrahydrofuran or acetonitrile, at temperatures between −40° C. and 110° C.

Working up according to process variants (A) and (B) is carried out by customary methods, for example by extracting products from the reaction mixture, which is diluted with water, using methylene chloride or toluene, washing the organic phase with water, drying and distilling or so-called "incipient distilling", i.e., by relatively long heating under reduced pressure at moderately increased temperatures, in order to free the product from the last volatile constituents.

A further purification can be effected by chromatography on silica gel using for example hexane:acetone=7:3 as the eluent.

The refractive index, melting point, Rf value or boiling point serve to characterize the compounds.

The compounds of the formula (III), (V), (VI) and (VII), to be used according to process variant (A) and (B) are generally known compounds of organic chemistry.

The action of the repellents of the general formula (I) is long-lasting.

They can thus be used with good success for repulsing noxious or unpleasant, sucking and biting insects and mites.

The sucking insects essentially encompass the common gnats (for example Aedes, Culex and Anopheles species), moth gnats (Phlebotomi), biting midges (Culicoides species), sandflies (Simulium species), biting flies (for example Stomoxys calcitrans), tsetse flies (Glossina species), horseflies (Tabanus, Haematopota and Chrysops species), houseflies (for example *Musca domestica* and *Fannia canicularis*), flesh-flies (for example *Sarcophaga carnaria*), flies causing myiasis (for example *Lucilia cuprina, Chrysomyia chloropyga, Hypoderma bovis, Hypoderma lineatum, Dermatobia hominis, Oestrus ovis, Gasterophilus intestinalis, Cohliomyia hominovorax*), bugs (for example *Cimex Lectularius, Rhodnius prolixus, Triatoma infestans*), lice (for example *Pediculus humanus, Haematopinus suis, Damalina oris*), keds (for example *Melaphagus orinus*), fleas (for example *Pulex irritans, Cthenocephalides canis, Xenopsylla cheopis*) and sand fleas (for example *Dermatophilus penetrans*).

The biting insects essentially comprise cockroaches (for example *Blattella germanica, Periplaneta americana, Blatta orientalis, Supella supellectilium*), beetles (for example *Sitophilus granarius, Tenebrio molitor, Dermestes lardarius, Stegobium paniceum, Anobium puntactum, Hylotrupes bajulus*), termites (for example *Reticulitermes lucifugus*) and ants (for example *Lasius niger*).

The mites include ticks (for example *Ornithodorus moubata, Ixodes ricinus, Boophilus microplus, Amblyomma hebreum*) and mites in the narrower sense (for example *Sarcoptres scabiei, Dermanyssus gallinae*).

The active compounds according to the invention, which can be employed undiluted or preferably diluted, may be converted into the formulations customary for repellents. They can be employed in all application forms customary in cosmetics, for example in the form of solutions, emulsions, gels, ointments, pastes, creams, powders, sticks, sprays or aerosols from spray cans.

For the use in the non-cosmetic area, the active compounds can be incorporated into granules, oil-based sprays or slow-release formulations.

The preparations are prepared in a known manner by mixing or diluting of the active compounds according to the invention with solvents (for example xylene, chlorobenzenes, paraffins, methanol, ethanol, isopropanol, water), carriers (for example kaolins, clays, talc, chalk, highly-disperse silica, silicates), emulsifiers (for example polyoxyethylene-fatty acid esters, polyoxyethylene-fatty alcohol ethers, alkyl sulphonates, aryl sulphonates) and dispersing agents (for example ligninsulphite waste liquors, methylcellulose).

In the formulations, the active compounds according to the invention can be mixed with each other or as mixtures with other known active compounds (for example sunscreen agents). In general, the preparations contain between 0.1 and 95% by weight of active compound, preferably between 0.5 and 90%.

For protection against blood-sucking insects or mites, the active compounds according to the invention are applied to the human or animal skin, or garments and other objects are treated with them.

The active compounds according to the invention are also suitable as additives to impregnating agents, for example for textile webs, garments, packaging materials and as additives for polishing agents, cleansing agents and window-cleaning agents.

The examples below of the preparations and the use of the active compounds according to the invention serve to further illustrate the invention.

EXAMPLE 1

A repellent in the form of a lotion for application on the skin is prepared by mixing 30 parts of one of the active compounds according to the invention, 1.5 parts of perfume and 68.5 parts of isopropanol. Isopropanol can be replaced by ethanol.

EXAMPLE 2

A repellent in the form of an aerosol for spraying onto the skin is prepared by formulating 50% of active compound solution, consisting of 30 parts of one of the active compounds according to the invention, 1.5 parts of perfume and 68.5 parts of isopropanol with 50% of Frigen 11/12 (=halogenated hydrocarbon as propellant) as a spraycan preparation.

EXAMPLE 3

Another spray can is composed of 40% of active-compound solution, consisting of 20 parts of one of the active compounds according to the invention, 1 part of perfume, 79 parts of isopropanol and 60% propane/butane (ratio 15:85).

Individual formulations were prepared following Examples 1, 2 and 3, using the active compounds below: compounds according to Preparation Examples Nos. 6 and 35.

The following examples of the biological action show that the substances according to the invention are superior compared with the prior art (diethyltoluamide=-DEET):

EXAMPLE A

Repellent test on guineapigs

Test animal: *Aedes aegypti*
Number of test animals: approx. 5,000
Solvent: Ethanol (99.8%)
3 parts by weight of active compound are taken up in 100 parts by volume of solvent.

A guineapig whose back has been shaved over an area of 50 cm² is fixed in a narrow cage (box) so that the mosquitoes have access only to the shaved area. The area is treated with 0.4 ml of active-compound solution, the solvent is allowed to evaporate, and the guineapig plus box are then placed into a cage of dimensions 60×60×60 cm containing test animals of the two sexes, which have only been fed sugar water.

The guineapig is watched for 10 minutes and the number of mosquitoes by which it is bitten is recorded. The guineapig is then removed, and the test is repeated after one hour. The experiment is carried out for a maximum of 9 hours or until the action stops.

In this test, for example the following compounds of the Preparation Examples show a superior action compared with the prior art (diethyltoluamide=DEET).

| Example A Repellent test on guineapigs | | |
|---|---|---|
| | Number of bites after: | |
| Active compound | 0–6ʰ | 7–9ʰ |
| (structure: m-methyl benzamide, C(O)–N(C₂H₅)₂) (known) | 2.0 | 13.7 |
| H₃C–C(O)–N(C₄H₉)–CH₂–C(O)–O–C₄H₉ (6) | 0 | 0.7 |
| H–C(O)–N(CH₂–CH=CH–CH₃)–C(CH₂–CH₂)–C(O)–O–C₂H₅ (35) | 1.3 | 4.7 |

PREPARATION EXAMPLES

Example 1

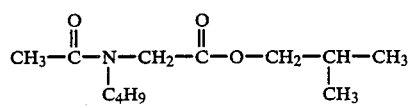

4.7 g (0.025 mol) of 2-methylpropyl N-butylaminoacetate and 10 ml of triethylamine are dissolved in 100 ml of tetrahydrofuran, and 5 ml of acetyl chloride are added at 20° C. to the mixture. The mixture is stirred at 20° C. for 8 hours, extracted using methylene chloride/water, dried and subjected to rotary evaporation. After filtration over silica gel (eluent=hexane:acetone=7:3), 5.3 g (approx. 92% of theory) of 2-methylpropyl N-acetyl-N-butyl-aminoacetate of refractive index $n_D^{20} = 1.4490$ are obtained.

Example 2

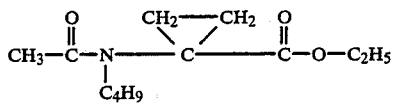

3.4 g (0.02 mol) of ethyl 1-acetylamino-cyclopropane-1-carboxylate are dissolved in 50 ml of tetrahydrofuran, and 0.72 g (0.024 mol) of sodium hydride (80% strength in paraffin) are added. The mixture is refluxed for 8 hours, and 3.3 g of n-butyl bromide (0.024 mol) are then added at 20° C. to the vigorously stirred solution. The mixture is heated at reflux temperature for 2 hours and cooled, and 50 ml of ammonium chloride solution are added to the reaction mixture. It is then extracted using methylene chloride, dried using magnesium sulphate, subjected to rotary evaporation and distilled.

1.3 g of ethyl N-acetyl-N-butyl-1-amino-cyclopropane-1-carboxylate (approx. 29% of theory) of boiling point 117° C./1 mbar are obtained.

The Preparation Examples 3 to 36 which are listed in Table 1 below are synthesized in analogy to the previously mentioned Preparation Examples 1 and 2.

$$\underset{R^2}{\overset{\underset{\displaystyle R^1}{\overset{\displaystyle O}{\underset{\displaystyle \|}{C}}}-\underset{\displaystyle |}{N}-\underset{\displaystyle \underset{\displaystyle O}{\|}}{\overset{\displaystyle R^3}{\underset{\displaystyle C}{}}\overset{\displaystyle R^4}{\underset{\displaystyle C}{}}}O-R^5}{}} \tag{I}$$

| Ex. No. | R¹ | R² | R³ | R⁴ | R⁵ | Physical Data |
|---|---|---|---|---|---|---|
| 3 | $C_2H_5$ | $C_4H_9$ | H | H | $C_2H_5$ | $n_D^{20} = 1.4500$ |
| 4 | $C_4H_9$ | $CH_3$ | —$CH_2$—$CH_2$— | | $C_2H_5$ | b.p. 90-93° C./0.15 mbar |
| 5 | $CH_3$ | $C_4H_9$ | H | H | $C_3H_7$-i | $n_D^{20} = 1.4405$ |
| 6 | $CH_3$ | $C_4H_9$ | H | H | $C_4H_9$ | $n_D^{20} = 1.4506$ |
| 7 | $CH_3$ | $C_4H_9$ | H | H | $CH_2\underset{\underset{CH_3}{\|}}{CH}C_2H_5$ | $n_D^{20} = 1.4515$ |
| 8 | $CH_3$ | $C_4H_9$ | H | H | $CH_2CH(C_2H_5)_2$ | $n_D^{20} = 1.4555$ |
| 9 | $CH_3$ | $C_4H_9$ | H | H | $\underset{\underset{CH_3}{\|}}{CH}CH_2CH(CH_3)_2$ | $n_D^{20} = 1.4481$ |
| 10 | $CH_3$ | $C_4H_9$ | H | H | $CH_2CH_2CH(CH_3)_2$ | $n_D^{20} = 1.4509$ |
| 11 | $CH_3$ | $C_4H_9$ | H | H | $CH_2CH=CH_2$ | $n_D^{20} = 1.4625$ |
| 12 | $CH_3$ | $C_4H_9$ | $CH_3$ | H | $C_4H_9$ | $n_D^{20} = 1.4507$ |
| 13 | $CH_3$ | $C_4H_9$ | H | H | $C_2H_5$ | $n_D^{20} = 1.4502$ |
| 14 | $C_4H_9$ | $CH_3$ | H | H | $C_4H_9$ | $n_D^{20} = 1.4514$ |
| 15 | $CH_3$ | $CH_3$ | —$(CH_2)_5$— | | $C_2H_5$ | $n_D^{20} = 1.4854$ |
| 16 | $CH_3$ | $CH_3$ | —$(CH_2)_5$— | | $C_4H_9$ | $n_D^{20} = 1.4811$ |
| 17 | H | $CH_3$ | —$CH_2$—$CH_2$— | | $CH_3$ | b.p.: 80-90° C. 0.2 mbar |
| 18 | H | $C_2H_5$ | —$CH_2$—$CH_2$— | | $C_2H_5$ | $n_D^{20}$: 1.4507 |
| 19 | H | $CH_3$ | —$CH_2$—$CH_2$— | | $C_2H_5$ | $n_D^{20}$: 1.4522 |
| 20 | H | $C_3H_7$ | —$CH_2$—$CH_2$— | | $C_2H_5$ | $n_D^{20}$: 1.4502 |
| 21 | H | $CH_3$ | —$CH_2$—$CH_2$— | | $C_3H_7$ | $n_D^{20} = 1.4510$ |
| 22 | H | $CH_3$ | —$CH_2$—$CH_2$— | | $C_4H_9$ | $n_D^{20} = 1.4475$ |
| 23 | H | $CH_3$ | —$CH_2$—$CH_2$— | | $C_4$—$H_9$-i | $n_D^{20} = 1.4481$ |
| 24 | H | $CH_3$ | —$CH_2$—$CH_2$— | | $C_5H_{11}$ | |
| 25 | H | $CH_3$ | —$CH_2$—$CH_2$— | | $CH_2$—$C_5H_{11}$ | b.p. 110-105° C./0.07 mbar |
| 26 | H | $CH_3$ | —$CH_2$—$CH_2$— | | $CH_2$—$C_7H_{15}$ | b.p. 110-105° C./0.2 mbar |
| 27 | H | $CH_3$ | —$CH_2$—$CH_2$— | | $CH_2-\underset{\underset{C_2H_5}{\|}}{CH}-C_2H_5$ | b.p. 102-105° C./0.05 mbar |
| 28 | H | $CH_3$ | —$CH_2$—$CH_2$— | | $C_4H_9$-t | $n_D^{20} = 1.4478$ |
| 29 | H | $CH_3$ | —$CH_2$—$CH_2$— | | $C_{10}H_{21}$ | b.p. 110-120° C./0.02 mbar |
| 30 | H | $CH_3$ | —$CH_2$—$CH_2$— | | $CH_2-\underset{\underset{CH(CH_3)_2}{\|}}{CH_2}$ | b.p. 80-90/0.4 mbar |
| 31 | H | $CH_3$ | —$CH_2$—$CH_2$— | | $CH-\underset{\underset{C_2H_5}{\|}}{CH}-C_4H_9$ | b.p. 90-100° C. 0.1 mbar |
| 32 | H | $CH_3$ | —$CH_2$—$CH_2$— | | $C_9H_{19}$ | b.p. 105-110° C./ |

-continued $$R^1-\overset{O}{\underset{}{C}}-\underset{\underset{R^2}{|}}{N}-\underset{\underset{O}{||}}{\overset{R^3}{C}}\overset{R^4}{\underset{}{}}-\overset{}{\underset{O}{C}}-O-R^5 \quad (I)$$

| Ex. No. | $R^1$ | $R^2$ | $R^3$ $R^4$ | $R^5$ | Physical Data |
|---|---|---|---|---|---|
| 33 | H | $C_4H_9$ | $-CH_2-CH_2-$ | $C_2H_5$ | 0.2 mbar b.p. 80–90° C./ 0.2 mbar |
| 34 | H | $CH_2-CH=CH_2$ | $-CH_2-CH_2-$ | $C_2H_5$ | $n_D^{20} = 1.4702$ |
| 35 | H | $CH_2-CH=CH$ <br> \| <br> $CH_3$ | $-CH_2-CH_2-$ | $C_2H_5$ | b.p. 95–100° C./ |
| 36 | H | $C_5H_{11}$ | $-CH_2-CH_2-$ | $C_2H_5$ | $n_D^{23} = 1.4496$ |

Preparation of the Precursors:

2-Methylpropyl N-butylaminoacetate 20 g (0.27 mol) of n-butylamine are dissolved in 100 ml of acetonitrile, and 7.8 g (0.04 mol) of 2-methylpropyl bromoacetate are added at 20° C. The mixture is stirred for 2 hours at 20° C. and subjected to rotary evaporation, the residue is taken up in methylene chloride/water, the organic phase is dried and subjected to rotary evaporation, and the residue is filtered over silica gel (eluent hexane:acetone=7:3). 5.3 g (71% of theory) of 2-methyl-propyl N-butylaminoacetate are obtained.

2-Methyl-propyl bromoacetate 41 g (0.2 mol) of bromoacetyl bromide are dissolved in 400 ml of tetrahydrofuran, and a mixture of 36 ml of triethylamine and 15 g of sec-butanol, dissolved in 20 ml of tetrahydrofuran, is added at 20° C. The mixture is stirred at 20° C. for 8 hours and extracted using water/methylene chloride. After drying, rotary evaporation and distillation, 13.9 g (36% of theory) of 2-methyl-propyl bromoacetate are obtained.

Ethyl 1-acetylamino-cyclopropanecarboxylate 96.2 g (0.7 mol) of 1-amino-cyclopropanecarboxylic acid hydrochloride are dissolved in 700 ml of ethanol and refluxed while hydrogen chloride is passed in. After 2.5 hours, the mixture is cooled and subjected to rotary evaporation, the residue is taken up in water, a pH of 8–9 is set using sodium hydrogen carbonate, and the mixture is extracted using methylene chloride. The organic phase is dried, subjected to rotary evaporation and distilled.

39 g (43% of theory) of ethyl 1-amino-cyclopropanecarboxylate of boiling point 33° C./0.3 mbar are obtained.

3.9 g (0.03 mol) of this compound are mixed with 6 ml of triethylamine and 50 ml of tetrahydrofuran, and 3.2 ml of acetyl chloride are added at 20° C. The mixture is stirred at 20° C. for 8 hours and extracted using methylene chloride/water, the organic phase is dried and subjected to rotary evaporation, and the residue is distilled using a bulb-tube furnace.

4.1 g (80% of theory) of ethyl 1-acetylamino-cyclopropanecarboxylate of boiling point 150° C./0.2 mbar are obtained.

What is claimed is:

1. An insect and mite repellent composition comprising a repellent effective amount of at least one acylated α-amino acid ester derivative of the formula $$R^1-\overset{O}{\underset{}{C}}-\underset{\underset{R^2}{|}}{N}-\underset{\underset{O}{||}}{\overset{R^3}{C}}\overset{R^4}{\underset{}{}}-\overset{}{\underset{O}{C}}-O-R^5$$

in which $R^1$ is hydrogen or for an unsubstituted or substituted alkyl, alkenyl or alkinyl radical, $R^2$ and $R^5$ are identical or different and are an unsubstituted or substituted alkyl, alkenyl or alkinyl radicals and $R^3$ and $R^4$ are hydrogen or an unsubstituted or substituted alkyl, aralkyl or aryl, or $R^3$ and $R^4$ together with the atom to which they are bonded form an unsubstituted or substituted, monocyclic ring in combination with a suitable extender.

2. A repellent composition according to claims 1, in which $R^1$ is hydrogen, $(C_1-C_{10})$-alkyl, $(C_2-C_{10})$-alkenyl or $(C_2-C_{10})$-alkinyl, $R^2$ and $R^5$ each independently are $(C_1-C_{10})$-alkyl, $(C_2-C_{10})$-alkenyl or $(C_2-C_{10})$-alkinyl and $R^3$ and $R^4$ are hydrogen, $(C_1-C_{10})$-alkyl, or aryl or aralkyl, each of which is unsubstituted or substituted in the aryl moiety by one to three identical or different substituents, and each of which has 6 to 10 carbon atoms in the aryl moiety and the alkyl of the aralkyl moiety has 1 to 4 carbon atoms wherein the aryl substituents in each case are selected from the group consisting of halogen, straight-chain or branched $(C_1-C_4)$-alkyl, $(C_1-C_4)$-halogenoalkyl, $(C_1-C_4)$-halogenoalkoxy and $(C_1-C_4)$-halogenoalkylthio, or, together $R^3$ and $R^4$ with the atom to which they are bonded, form a cycloalkyl having 3 to 7 carbon atoms.

3. A repellent composition according to claim 1, in which $R^1$ is hydrogen, $(C_1-C_5)$-alkyl, $(C_2-C_5)$-alkenyl or $(C_2-C_5)$-alkinyl, $R^2$ is $(C_1-C_5)$-alkyl, $(C_2-C_5)$-alkenyl or $(C_2-C_5)$-alkinyl, $R^3$ and $R^4$ are hydrogen, $(C_1-C_5)$-alkyl, for phenyl or phenylalkyl which has 1 or 2 carbon atoms in the alkyl moiety and each of which is unsubstituted or substituted by one to three identical or different substituents, selected from the group consisting of fluorine, chlorine, bromine, $(C_1-C_2)$-alkyl, $(C_1-C_2)$-halogenoalkyl, $(C_1-C_2)$-halogenoalkoxy, and $(C_1-C_2)$-halogenoalkylthio or, $R^3$ and $R^4$ together with the atom to which they are bonded, form cycloalkyl having 3 to 6 carbon atoms and $R^5$ is $(C_1-C_{10})$-alkyl, $(C_2-C_5)$-alkenyl or $(C_2-C_5)$-alkinyl.

4. A repellent composition according to claim 1, in which $R^1$ is hydrogen, $(C_1-C_5)$-alkyl, $(C_2-C_5)$-alkenyl or $(C_2-C_5)$-alkinyl, $R^2$ is $(C_1-C_5)$-alkyl, $(C_2-C_5)$-alkenyl or $(C_2-C_5)$-alkinyl, $R^3$ and $R^4$ are hydrogen or $(C_1-C_5)$-alkyl, or phenyl, benzyl or phenethyl, each of which is unsubstituted or substituted in the phenyl moiety by one to three identical or different substituents, selected from the group consisting of fluorine, chlorine, bromine, methyl, ethyl, trifluoromethyl, trifluoromethoxy and trifluoromethylthio or $R^3$ and $R^4$ together with the atom to which they are bonded form a cyclopropyl, cyclopentyl or cyclohexyl and $R^5$ stands for $(C_1-C_{10})$-alkyl, $(C_2-C_5)$-alkenyl or $(C_2-C_5)$-alkinyl.

5. A repellent composition according to claim 1, in which $R^1$ is hydrogen, $(C_1-C_5)$-alkyl or $(C_2-C_5)$-alkenyl, $R^2$ is $(C_1-C_5)$-alkyl or $(C_2-C_5)$-alkenyl, $R^3$ and $R^4$ are hydrogen or $(C_1-C_5)$-alkyl or $R^3$ and $R^4$ together with the atom to which they are bonded form a cyclopropyl and $R^5$ is $(C_1-C_5)$-alkyl or $(C_2-C_5)$-alkenyl.

6. A method for repelling insects and mites comprising applying to surfaces to which insects and mites are attracted an effective repelling amount of at least one acylated α-amino acid ester according to claim 1.

* * * * *